(12) United States Patent
Centeno

(10) Patent No.: US 9,168,261 B2
(45) Date of Patent: Oct. 27, 2015

(54) COMPOSITIONS AND METHODS FOR CARTILAGE REPAIR

(71) Applicant: Regenerative Sciences, LLC, Broomfield, CO (US)

(72) Inventor: Christopher J. Centeno, Broomfield, CO (US)

(73) Assignee: Regenerative Sciences, LLC, Broomfield, CO (US)

( * ) Notice: Subject to any disclaimer, the term of this patent is extended or adjusted under 35 U.S.C. 154(b) by 0 days.

(21) Appl. No.: 13/931,572

(22) Filed: Jun. 28, 2013

(65) Prior Publication Data

US 2013/0287753 A1   Oct. 31, 2013

Related U.S. Application Data

(63) Continuation of application No. 12/922,436, filed as application No. PCT/US2009/037126 on Mar. 13, 2009, now abandoned.

(60) Provisional application No. 61/036,551, filed on Mar. 14, 2008.

(51) Int. Cl.
| | |
|---|---|
| A61P 19/02 | (2006.01) |
| A61K 35/19 | (2015.01) |
| A61K 35/28 | (2015.01) |
| A61K 31/56 | (2006.01) |
| A61K 31/573 | (2006.01) |
| A61K 31/19 | (2006.01) |
| A61K 31/375 | (2006.01) |
| A61K 31/7088 | (2006.01) |
| A61K 35/16 | (2015.01) |
| A61K 38/18 | (2006.01) |
| A61K 38/20 | (2006.01) |
| A61K 38/36 | (2006.01) |
| A61K 45/06 | (2006.01) |

(52) U.S. Cl.
CPC ............. *A61K 31/56* (2013.01); *A61K 31/19* (2013.01); *A61K 31/375* (2013.01); *A61K 31/573* (2013.01); *A61K 31/7088* (2013.01); *A61K 35/16* (2013.01); *A61K 35/19* (2013.01); *A61K 35/28* (2013.01); *A61K 38/1825* (2013.01); *A61K 38/1841* (2013.01); *A61K 38/1875* (2013.01); *A61K 38/2006* (2013.01); *A61K 38/363* (2013.01); *A61K 45/06* (2013.01); *A61L 2300/222* (2013.01)

(58) Field of Classification Search
None
See application file for complete search history.

(56) References Cited

U.S. PATENT DOCUMENTS

| | | |
|---|---|---|
| 5,145,676 A | 9/1992 | Fahey et al. |
| 5,165,938 A | 11/1992 | Knighton |
| 5,197,985 A | 3/1993 | Caplan et al. |
| 5,198,357 A | 3/1993 | Holmovist et al. |
| 5,226,914 A | 7/1993 | Caplan et al. |
| 5,486,359 A | 1/1996 | Caplan et al. |
| 5,736,396 A | 4/1998 | Bruder et al. |
| 5,749,874 A | 5/1998 | Schwartz |
| 5,769,899 A | 6/1998 | Schwartz et al. |
| 5,770,215 A | 6/1998 | Moshyedi |
| 5,842,477 A | 12/1998 | Naughton et al. |
| 6,200,606 B1 | 3/2001 | Peterson et al. |
| 6,387,367 B1 | 5/2002 | Davis-Sproul et al. |
| 6,530,956 B1 | 3/2003 | Mansmann |
| 6,623,733 B1 | 9/2003 | Hossainy et al. |
| 6,699,471 B2 | 3/2004 | Marco et al. |
| 6,699,484 B2 | 3/2004 | Whitmore et al. |
| 6,835,377 B2 | 12/2004 | Goldberg et al. |
| 6,872,567 B2 | 3/2005 | Thomas et al. |
| 7,229,959 B1 | 6/2007 | Drohan et al. |
| 8,088,119 B2 | 1/2012 | Saal et al. |
| 8,277,437 B2 | 10/2012 | Saal et al. |
| 2002/0110544 A1 | 8/2002 | Goldberg et al. |
| 2003/0050709 A1 | 3/2003 | Noth et al. |
| 2003/0224411 A1 | 12/2003 | Stanton et al. |
| 2004/0078077 A1 | 4/2004 | Binette et al. |
| 2004/0136968 A1 | 7/2004 | Zheng et al. |
| 2004/0229786 A1 | 11/2004 | Attawia et al. |
| 2004/0229878 A1 | 11/2004 | DiMauro et al. |
| 2004/0235166 A1 | 11/2004 | Prockop et al. |
| 2005/0019865 A1* | 1/2005 | Kihm et al. .................. 435/69.1 |
| 2005/0038520 A1 | 2/2005 | Binette et al. |
| 2005/0100536 A1 | 5/2005 | Mishra |
| 2005/0118230 A1 | 6/2005 | Hill et al. |
| 2005/0205498 A1 | 9/2005 | Sowemimo-Coker et al. |
| 2005/0276792 A1 | 12/2005 | Kaminski et al. |
| 2006/0073124 A1 | 4/2006 | Garcia Castro et al. |
| 2006/0128016 A1 | 6/2006 | Tokushima et al. |
| 2006/0275273 A1 | 12/2006 | Seyedin et al. |

(Continued)

FOREIGN PATENT DOCUMENTS

| | | |
|---|---|---|
| EP | 2257176 | 9/2013 |
| KR | 2003 024028 | 3/2003 |

(Continued)

OTHER PUBLICATIONS

Lee et al., Blood, 2004, vol. 103(5):1669-1675.*
Ries et al. (2007) Blood 109(9):4055-4063 "MMP-2, MT1-MMP, and TIMP-2 are essential for the invasive capacity of human mesenchymal stem cells: differential regulation by inflammatory cytokines".
Bosnakovski et al., "Chondrogenic differentiation of bovine bone marrow mesenchymal stem cells (MSCs) in different hydrogels: influence of collagen type II extracellular matrix on MSC chondrogenesis" Biotechnology Bioeng., (2006) 96(6): 1152-63.
Chrisman, O.D., The effect of growth hormone on established cartilage lesions. A presidential address to the Association of Bone and Joint Surgeons, 1974. Clin Orthop Relat Res., (1975) 107:232-8.

(Continued)

*Primary Examiner* — Xiaozhen Xie

(74) *Attorney, Agent, or Firm* — Swanson & Bratschun, L.L.C.

(57) ABSTRACT

Autologous compositions and methods are provided for cartilage repair in patients in need thereof. Some aspects include combinations of platelet-based materials with chondrogenesis inducing agents in the presence or absence of cell-based therapies.

6 Claims, No Drawings

(56) References Cited

U.S. PATENT DOCUMENTS

| | | | |
|---|---|---|---|
| 2007/0087032 | A1 | 4/2007 | Chang et al. |
| 2007/0122904 | A1 | 5/2007 | Nordon |
| 2007/0128722 | A1 | 6/2007 | Lin et al. |
| 2007/0280959 | A1* | 12/2007 | Meury et al. ............... 424/198.1 |
| 2008/0038233 | A1 | 2/2008 | Freemont et al. |
| 2009/0010896 | A1 | 1/2009 | Centeno et al. |
| 2009/0208464 | A1 | 8/2009 | Centeno |
| 2009/0274665 | A1 | 11/2009 | Akabutu et al. |
| 2010/0168022 | A1 | 7/2010 | Centeno |
| 2011/0052533 | A1 | 3/2011 | Centeno |
| 2011/0054929 | A1 | 3/2011 | Centeno |
| 2011/0200642 | A1 | 8/2011 | Centeno |
| 2011/0245804 | A1 | 10/2011 | Centeno |
| 2013/0084341 | A1 | 4/2013 | Centeno |
| 2013/0108593 | A1 | 5/2013 | Centeno |

FOREIGN PATENT DOCUMENTS

| | | |
|---|---|---|
| WO | WO 97/34614 | 9/1997 |
| WO | WO 98/51317 | 11/1998 |
| WO | WO 01/80865 | 11/2001 |
| WO | WO 2004/067704 | 8/2004 |
| WO | WO 2005/046761 | 5/2005 |
| WO | WO 2005/085421 | 9/2005 |
| WO | WO 2007/087519 | 8/2007 |
| WO | WO 2008/034803 | 3/2008 |
| WO | WO 2009/006161 | 1/2009 |
| WO | WO 2009/085969 | 7/2009 |
| WO | WO 2009/114785 | 9/2009 |
| WO | WO 2009/124192 | 10/2009 |
| WO | WO 2010/065854 | 6/2010 |

OTHER PUBLICATIONS

Denko et al., "Role of the growth hormone/insulin-like growth factor-1 paracrine axis in rheumatic diseases" Semin Arthritis Rheum, (2005) 35(1): 24-34.

Derfoul et al., "Glucosamine promotes chondrogenic phenotype in both chondrocytes and mesenchymal stem cells and inhibits MMP-13 expression and matrix degradation" Osteoarthritis Cartilage (2007) 15(6):646-55.

Johnson et al., "Integrative Repair of Cartilage with Articular and Nonarticular Chondrocytes" Tissue Engineering, (2004) 10(9-10): 1308-1318.

Kawamura et al., "Adenoviral-mediated transfer of TGF-beta1 but not IGF-1 induces chondrogenic differentiation of human mesenchymal stem cells in pellet cultures" Exp Hematol., (2005) 33(8):865-72.

Landesberg et al. J. Oral Maxillogac Sur "Quantification of growth factor levels using a simplified method of platelet-rich plasma gel preparation" 58:297 (2000).

Miyata et al., "Platelet-derived growth factor-BB (PDGF-BB) induces differentiation of bone marrow endothelial progenitor cell-derived cell line TR-BME2 into mural cells, and changes the phenotype" J Cell Physiol. (2005) 204(3): 948-55.

Song et al., "Mesenchymal stem cell-based cartilage tissue engineering: cells, scaffold and biology"Cytotherapy (2004) 6(6):596-601.

Toh W. S., et al., "Combined effects of TGFbeta1 and BMP2 in serum-free chondrogenic differentiation of mesenchymal stem cells induced hyaline-like cartilage formation" Growth Factors (2005) 23(4): 313-21.

Zhang et al., "In vitro chondrogenic phentotype differnetiation of bone marrow-derived mesnchymal stem cells" J. Huazhong Univ Sci Technology Med Sci., (2004) 24(3): 275-8.

Zhu et al., "The Role of the Hyaluronan Receptor CD44 in MSC Migration in the Extracellular Matrix" Stem Cell (2005) vol. 24 (4) pp: 928-35.

PR Newswire (2013) "NeuroTherm Acquires Smith & Nephew Interventional Spine Pain Management Assets" Database [Online] Apr. 7. Available Web Site: http://www.prnewswire.com/news-releases/neurotherm-acquires-smith--nephew-interventional-spine-pain-management-assets-89991457.html Last Update: Unknown Accessed on: Nov. 21, 2013.

Smith & Nephew Home Page (2009) "Smith & Nephew launches TRUCATH Spinal Injection System" Database [Online] Sep. 28. Available Web Site: http://www.smith-nephew.com/new-and-media/news/smith-and-nephew-launches-trucath-spinal-incetio/ Last Update: Unknown Accessed on: Nov. 21, 2013.

Acosta et al (2005) "The Potential Role of Mesenchymal Stem Cell Therapy for Intervertebral Disc Degeneration: A Critical Overview" Neurosurg. Focus 19(3):E4.

Ahuja et al (1995) "Identification of Two Subpopulations of Rat Monocytes Expressing Disparate Molecular Forms and Quantities of CD43" Cell Immunol. 163(1):59-69.

Alhadlaq and Mao (2004) "Mesenchymal Stem Cells: Isolation and Therapeutics" Stem Cells Dev. 13(4):436-448.

Ando et al (2007) "Cartilage repair using an in vitro generated scaffold-free tissue-engineered construct derived from porcine synovial mesenchymal stem cells" Biomaterials 1-9. Available Website: www.sciencedirect.com.

Anitua et al (2004) "Autologous Platelets as a Source of Proteins for Healing and Tissue Regeneration" Thromb. Haemost. 91:4-15.

Avascular Necrosis in patient education of Illinois Bone and Joint Institute. 2003 downloaded from the hipdoc.com/avas.htm. p. 1-2.

Baecher-Allan et al (2005) "Functional Analysis of Highly Defined, FACS-Isolated Populations of Human Regulatory CD4+CD25+ T Cells" Clinical Immunology 115:10-18.

Barry (2003) "Mesenchymal Stem Cell Therapy in Joint Disease" Novartis Found. Symp. 249:86-102, 170-4, 239-41.

Bensaïd et al (2003) "A Biodegradable Fibrin Scaffold for Mesenchymal Stem Cell Transplantation" Biomaterials 24:2497-2502.

Bernardo et al (2007) "Optimization of In Vitro Expansion of Human Multipotent Mesenchymal Stromal Cells for Cell-Therapy Approaches: Further Insights in the Search for a Fetal Calf Serum Substitute" J. Cell. Physiol. 211:121-130.

Billard et al (2000) "Switch in the Protein Tyrosine Phosphatase Associated with Human CD100 Semaphorin at Terminal B-Cell Differentiation Stage" Blood 95(3):965-972.

Bircher et al (1988) "Discitis Following Lumbar Surgery" Spine 13(1):98-102.

Borner and Follath (1989) "Antibiotic Therapy and Long-Term Outcome in Patients with Vertebral Osteomyelitis" Schweiz Med. Wochenschr. 119(1):19-21 (German, English Abstract Only).

Brisby et al (2004) "Cell Therapy for Disc Degeneration-Potentials and Pitfalls" Orthop. Clin. North Am. 35(1):85-93.

Buckwalter and Mankin (1998) "Articular Cartilage: Degeneration and Osteoarthritis, Repair, Regeneration, and Transplantation" AAOS Instr. Course Lect. 47:487-504.

Bühring et al (1999) "The Monoclonal Antibody 97A6 Defines a Novel Surface Antigen Expressed on Human Basophils and Their Multipotent and Unipotent Progenitors" Blood 94(7):2343-2356.

Caligiuri et al (1990) "Functional Consequences of Interleukin 2 Receptor Expression on Resting Human Lymphocytes. Identification of a Novel Natural Killer Cell Subset with High Affinity Receptors" J. Exp. Med. 171:1509-1526.

Caplan and Bruder (2001) "Mesenchymal Stem Cells: Building Blocks for Molecular Medicine in the 21st Century" Trends Mol. Med. 7(6):259-264.

Caplan (1991) "Mesenchymal Stem Cells" J. Orthop. Res. 9(5):641-650.

Cashman et al (1990) "Mechanisms that Regulate the Cell Cycle Status of Very Primitive Hematopoietic Cells in Long-Term Human Marrow Cultures. I. Stimulatory Role of a Variety of Mesenchymal Cell Activators and Inhibitory Role of TGF-Beta" Blood 75(1):96-101.

Cassiede et al (1996) "Osteochondrogenic Potential of Marrow Mesenchymal Progenitor Cells Exposed to TGF-β1 or PDGF-BB as Assayed In Vivo and In Vitro" J. of Bone and Miner. Res. 11(9):1264-1273.

Castro et al (2002) "Failure of Bone Marrow Cells to Transdifferentiate into Neutral Cells In Vivo" Science 297:1299.

(56) References Cited

OTHER PUBLICATIONS

Centeno et al (2006) "Partial Regeneration of the Human Hip Nucleated Cell Transfer: A Case Study" Pain Physician 9:253-256.
Centeno et al. (2008) The American Journal of Case Reports 9:201-206 "Increased Knee Cartilage Volume in Degenerative Joint Disease using Percutaneously Implanted, Autologous Mesenchymal Stem Cells, Platelet Lysate and Dexamethasone".
Centeno et al (2008) Medical Hypotheses 71:900-908 "Regeneration of meniscus cartilage in a knee treated with percutaneously implanted autologous mesenchymal stem cells".
Centeno et al. (2008) Pain Physician 11(3):343-353 "Increased Knee Cartilage Volume in Degenerative Joint Disease using Percutaneously Implanted, Autologous Mesenchymal Stem Cells".
Centeno et al. (2011) Bioengineering & Biomedical Science S2:007 "A Case Series of Percutaneous Treatment of Non-Union Fractures with Aulogous, Culture Expanded, Bone Marrow Derived, Mesenchymal Stem Cells and Platelet Lysate".
Centeno and Faulkner (2012) "The Use of Mesenchymal Stem Cells in Orthopedics" Stem Cells and Cancer Stem Cells 1:173-179.
Charalambous et al (2003) "Septic Arthritis Following Intra-Articular Steroid Injection of the Knee—a Survey of Current Practice Regarding Antiseptic Technique used During Intra-Articular Steroid Injection of the Knee" Clin. Rheumatol. 22:386-390.
Chazerain et al (1999) "Septic Hip Arthritis After Multiple Injections into the Joint of Hyaluronate and Glucocorticoid" Rev. Rhum. Engl. Ed. 66(7-9):436-437.
Crisostomo et al (2006) "High Passage Number of Stem Cells Adversely Affects Stem Cell Activation and Myocardial Protection" Shock 26(6):575-580.
D'Ippolito et al (1999) "Age-Related Osteogenic Potential of Mesenchymal Stromal Stem Cells from Human Verterbral Bone Marrow" J. Bone Miner. Res. 14(7):1115-122.
Dall et al (1987) "Postoperative Discitis. Diagnosis and Management" Clin. Orthop. Relat. Res. 224:138-146.
Del Curling et al (1990) "Changing Concepts in Spinal Epidural Abscess: A Report of 29 Cases" Neurosurgery 27(2):185-192.
Deschaseaux et al (2003) "Direct Selection of Human Bone Marrow Mesenchymal Stem Cells Using an Anti-CD49a Antibody Reveals Their $CD45^{med,low}$ Phenotype" British Journal of Haematology 122:506-517.
Doucet et al (2005) "Platelet Lysates Promote Mesenchymal Stem Cell Expansion: A Safety Substitute for Animal Serum in Cell-Based Therapy Applications" J. Cell. Physiol. 205:228-236.
Elghetany and Patel (2002) "Assessment of CD24 Expression on Bone Marrow Neutrophilic Granulocytes: CD24 is a Marker for the Myelocytic Stage of Development" Am. J. Hematol. 71:348-349.
Fang et al (2004) "Biocompatibility Studies on Fibrin Glue Cultured with Bone Marrow Mesenchymal Stem Cells In Vitro" J. of Huazhong. Univ. of Sci. Technolog. Med. Sci. 24(3):272-274.
Fiedler et al (2002) "BMP-2, BMP-4, and PDGF-bb Stimulate Chemotactic Migration of Primary Human Mesenchymal Progenitor Cells" J. Cell. Biochem. 87:305-312.
Fiedler et al (2004) "To Go or Not to Go: Migration of Human Mesenchymal Progenitor Cells Stimulated by Isoforms of PDGF" J. Cell. Biochem. 93:990-998.
Fortier et al (1998) "Isolation and Chondrocytic Differentiation of Equine Bone Marrow-Derived Mesenchymal Stem Cells" Am. J. Vet. Res. 59(9):1182-1187.
Fraser et al (1993) "Each Hypersensitive Site of the Human Beta-Globin Locus Control Region Confers a Different Developmental Pattern of Expression on the Globin Genes" Genes & Development 7:106-113.
Fujiwara et al (1994) "Acute Purulent Discitis with Epidural Abscess of the Cervical Spine in an Adult" Neurol. Med. Chir. (Tokyo) 34(6):382-384.
Gajdusek et al (1993) "Basic Fibroblast Growth Factor and Transforming Growth Factor Beta-1: Synergistic Mediators of Angiogenesis In Vitro" J. Cell. Physiol. 157(1):133-144.
Gazzit et al (1995) "Purified $CD34^+$ $Lin^-$ $Thy^+$ Stem Cells do Not Contain Clonal Myeloma Cells" Blood 86(1):381-389.

Gibson and Waddell (2005) "Surgery for Degenerative Lumbar Spondylosis: Updated Cochrane Review" Spine 30(20):2312-2320.
Gruber and Hanley (2003) "Recent Advances in Disc Cell Biology" Spine 28(2):186-193.
Gruber et al (2004) "Platelet-Released Supernatants Increase Migration and Proliferation, and Decrease Osteogenic Differentiation of Bone Marrow-Derived Mesenchymal Progenitor Cells Under In Vitro Conditions" Platelets 15(1):29-35.
Gustafson et al (1989) "Further Investigations into the Potentiation of Infection by Intra-Articular Injection of Polysulfated Glycosaminoglycan and the Effect of Filtration and Intra-Articular Injection of Amikacin" Am. J. Vet. Res. 50(12):2018-2022.
Hickstein et al (1992) "Identification of the Promoter of the Myelomonocytic Leukocyte Integrin CD11b" Proc. Natl. Acad. Sci. USA 89(6):2105-2109.
Hip Replacement Surgery. John Hopkins Medicine. Downloaded on Jul. 14, 2012 from www.hopkinsmedicine.org/healthlibrary/conditions/adult/orthopaedic_disorders/hip_replacement_surger_85, P01372. p. 1-4.
Hirschi et al (1999) "Endothelial Cells Modulate the Proliferation of Mural Cell Precursors Via Platelet-Derived Growth Factor-BB and Heterotypic Cell Contact" Circ. Res. 84(3):298-305.
Hoelscher et al (2000) "Effects of Very High Antibiotic Concentrations on Human Intervertebral Disc Cell Proliferation, Viability, and Metabolism In Vitro" Spine 25(15):1871-1877.
Huang and Terstappen (1994) "Formation of Haematopoietic Microenvironment and Haematopoietic Stem Cells from Single Human Bone Marrow Stem Cells" Nature 368(6472):664.
Huss (2000) "Perspectives on the Morphology and Biology of CD34-Negative Stem Cells" J. Hematother. Stem Cell Res. 9:783-793.
Iversen et al (1992) "Prognosis in Postoperative Discitis, A Retrospective Study of 111 Cases" Acta Orthop. Scand. 63(3):305-309.
Johnstone and Yoo (1999) "Autologous Mesenchymal Progenitor Cells in Articular Cartilage Repair" Clin. Orthop. Relat. Res. 367 Suppl:S156-162.
Kambin and Schaffer (1989) "Percutaneous Lumbar Discectomy Review of 100 Patients and Current Practice" Clin. Orthop. Relat. Res. 238:24-34.
Kang et al (2005) "Role of c-Jun N-Terminal Kinase in the PDGF-Induced Proliferation and Migration of Human Adipose Tissue-Derived Mesenchymal Stem Cells" J. Cell. Biochem. 95:1135-1145.
Kaps et al (2002) "Human Platelet Supernatant Promotes Proliferation but Not Differentiation of Articular Chondrocytes" Med. Biol. Eng. Comput. 40(4):485-490.
Katz et al (1987) "Effect of Platelet-Derived Growth Factor on Enriched Populations of Haemopoietic Progenitors from Patients with Chronic Myeloid Leukaemia" Leuk. Res. 11(4):339-344.
Kilian et al (2004) "Effects of Platelet Growth Factors on Human Mesenchymal Stem Cells and Human Endothelial Cells In Vitro" Eur. J. Med. Res. 9(7):337-344.
Kirshenbaum et al (1999) "Demonstration that Human Mast Cells Arise from a Progenitor Cell Population that is CD34+, c-kit+, and Expresses Aminopeptidase N (CD13)" Blood 94:2333-2342.
Kitoh et al (2004) "Transplantation of Marrow-Derived Mesenchymal Stem Cells and Platelet-Rich Plasma During Distraction Osteogenesis—a Preliminary Result of Three Cases" Bone 35:892-898.
Koga et al (2008) "Local adherent technique for transplanting mesenchymal stem cells as a potential treatment of cartilage defect" Arthritis Research & Therapy 10(R84), 1-10. Available web site: http://arthritis-research.com/content/10/4/R84 (Adherent Technique).
Koga et al (2008) "Local adherent technique for transplanting mesenchymal stem cells as a potential treatment of cartilage defect" Arthritis Research & Therapy 10(R84), 1-10. Available web site: http://arthritis-research.com/content/10/4/R84 (Novel Technique).
Koh et al (2005) "Co-Culture of Human CD34+ Cells with Mesenchymal Stem Cells Increases the Survival of CD34+ Cells Against the 5-Aza-Deoxycytidine- or Trichostatin A-Induced Cell Death" Biochem. Biophys. Res. Commun. 329:1039-1045.
Kortelainen and Särkioja (1990) "Fatal Complications of Intramuscular and Intra-Articular Injections" Z Rechtsmed. 103:547-554.

(56) References Cited

OTHER PUBLICATIONS

Kravitz et al. "How Do Muscles Grow", IDEA Fitness Journal; 3(2), 23-25 (2006) (http://www.unm.edu/'kravitz/Article%20folder/musclesgrowLK.html).

Laiho and Kotilainen (2001) "Septic Arthritis Due to Prevotella Bivia After Intra-Articular Hip Joint Injection" Joint Bone Spine 68:443-444.

Lange et al (2007) "Accelerated and Safe Expansion of Human Mesenchymal Stromal Cells in Animal Serum-Free Medium for Transplantation and Regenerative Medicine" Journal of Cellular Physiology 213(1):18-26.

Luis A. Solchaga et al (2002) "Treatment of Osteochondral Defects with Autologous Bone Marrow in a Hyaluronan-Based Delivery Vehicle", Tissue Engineering, vol. 8, No. 2, pp. 333-347.

Luyten (2004) "Mesenchymal Stem Cells in Osteoarthritis" Curr. Opin. Rheumatol. 16:599-603.

Magne et al (2005) "Mesenchymal Stem Cell Therapy to Rebuild Cartilage" Trends Mol. Med. 11(11):519-526.

Martineau et al (2004) "Effects of Calcium and Thrombin on Growth Factor Release from Platelet Concentrates: Kinetics and Regulation of Endothelial Cell Proliferation" Biomaterials 25:4489-4502.

Medina et al (2000) "Purification of Human Tonsil Plasma Cells: Pre-Enrichment Step by Immunomagnetic Selection of $CD31^+$ Cells" Cytometry 39(3):231-234.

Mezey et al and Castro et al (2003) "Comment on and Response to Comment on Failure of Bone Marrow Cells to Transdifferentiate into Neutral Cells In Vivo" Science 299:1184b-1184c.

Miyata et al (2005) "Platelet-Derived Growth Factor-BB (PDGF-BB) Induces Differentiation of Bone Marrow Endothelial Progenitor Cell-Derived Cell Line TR-BME2 into Mural Cells, and Changes the Phenotype" J. Cell. Physiol. 204:948-955.

Morshed et al (2004) "Septic Arthritis of the Hip and Intrapelvic Abscess Following Intra-Articular Injection of Hylan G-F 20. A Case Report" J. Bone Joint Surg. Am. 86:823-826.

Munirah et al (2008) "Autologous Versus Pooled Human Serum for Articular Chondrocyte Growth" Journal of Orthopedic Surgery 16(2):220-229.

Müller et al (2006) "Animal Serum-Free Culture Conditions for Isolation and Expansion of Multipotent Mesenchymal Stromal Cells from Human BM" Cytotherapy 8(5):437-444.

Murphy et al (2003) "Stem Cell Therapy in a Caprine Model of Osteoarthritis" Arthritis Rheum. 48(12):3464-3474.

Murray et al (1999) "CD109 is Expressed on a Subpopulation of $CD34^+$ Cells Enriched in Hematopoietic Stem and Progenitor Cells" Exp. Hematol. 27:1282-1294.

Nakayama et al (2000) "Evaluation of Glycosaminoglycans Levels in Normal Joint Fluid of the Knee" J. Nippon Med. Sch. 67(2)92-95.

Nielsen et al (1990) "Postoperative Discitis. Radiology of Progress and Healing" Acta Radiol. 31(6):559-563.

Olweus et al (1995) "CD64/Fc Gamma RI is a Granulo-Monocytic Lineage Marker on CD34+ Hematopoietic Progenitor Cells" Blood 85(9):2402-2413.

Onofrio (1980) "Intervertebral Discitis: Incidence, Diagnosis, and Management" Clin. Neurosurg. 27:481-516.

Ordog et al (2004) "Purification of Interstitial Cells of Cajal by Fluorescence-Activated Cell Sorting" Am. J. Physiol. Cell Physiol 286(2):448-456.

Orpen and Birch (2003) "Delayed Presentation of Septic Arthritis of a Lumbar Facet Joint after Diagnostic Facet Joint Injection" J. Spinal Disord. Tech. 16(3):285-287.

Oshima et al (2004) "Fate of Transplanted Bone-Marrow-Derived Mesenchymal Cells During Osteochondral Repair using Transgenic Rats to Simulate Autologous Transplantation" OsteoArthritis Cartilage 12:811-817.

Otawa et al (2000) "Comparative Multi-Color Flow Cytometric Analysis of Cell Surface Antigens in Bone Marrow Hematopoietic Progenitors Between Refractory Anemia and Aplastic Anemia" Leukemia Research 24:359-366.

Park et al (2005) "Thoughts and Progress, Tissue-Engineered Cartilage Using Fibrin/Hyaluronan Composite Gel and its In Vivo Implantation" Artif. Organs 29(10):838-860.

Pellaton et al (1981) "Spectic Arthritis Following Repeated Intraarticular Injections of Glycosaminoglycanpolysulfat (Arteparon®) and Steroids for Osteoarthrosis of the Knee Joint" (French, English Abstract Only) Schweiz. Rudnsch. Med. Prax. 70(52):2364-2367.

Pietramaggiori et al (2006) "Freeze-Derived Platelet-Rich Plasma Shows Beneficial Healing Properties in Chronic Wounds" Wound Rep. Reg. 14:573-580.

Ponte and McDonald (1992) "Septic Discitis Resulting from *Escherichia coli* Urosepsis" J. Fam. Pract. 34(6):767-771.

Prins et al (1982) "Effect of Purified Growth Factors on Rabbit Articular Chondrocytes in Monolayer Culture. II. Sulfated Proteoglycan Synthesis" Arthritis & Rheumatism, 25(10):1228-1238.

Rasmusson et al (2003) "Mesenchymal Stem Cells Inhibit the Formation of Cytotoxic T Lymphocytes, but Not Activated Cytotoxic T Lymphocytes or Natural Killer Cells" Transplantation 76(8):1208-1213.

Reddi and Cunningham (1990) "Bone Induction by Osteogenin and Bone Morphogenetic Proteins" Biomaterials 11:33-34.

Regenexx™ PR article published Nov. 8, 2007; downloaded May 14, 2012.

Richardson et al (2006) "Intervertebral Disc Cell-Mediated Mesenchymal Stem Cell Differentiation" Stem Cells 24:707-716.

Roberts et al (2003) "Autologous Chondrocyte Implantation for Cartilage Repair: Monitoring its Success by Magnetic Resonance Imaging and Histology" Arthritis Research and Therapy 5(1):R60-R73.

Rolf et al (1999) "Intra-Articular Absorption and Distribution of Ketoprofen After Topical Plaster Application and Oral Intake in 100 Patients Undergoing Knee Arthroscopy" Rheumatology 38:564-567.

Ruszymah (2004) "Autologous Human Fibrin as the Biomaterial for Tissue Engineering" Med. J. Malaysia 59 Suppl.B:30-1.

Sah et al "Effects of Fibrin Glue Components on Chondrocyte Growth and Matrix Formation," in 49th Annual Meeting of the Orthopaedic Research Society, poster #0721, (Feb. 2003).

Sanchez et al (2003) "Is Platelet-Rich Plasma the Perfect Enhancement Factor? A Current Review" Int. J. Oral Maxillofac. Implants 18:93-103.

Sato et al (1999) "Reversible Expression of CD34 by Murine Hematopoietic Stem Cells" Blood 94(8):2548-2554.

Schallmoser et al (2007) "Human Platelet Lysate Can Replace Fetal Bovine Serum for Clinical-Scale Expansion of Functional Mesenchymal Stromal Cells" Transfusion 47(8):1436-1446.

Silverman et al (Jun. 1999) "Injectable Tissue-Engineered Cartilage Using a Fibrin Glue Polymer" Plast. Reconstr. Surg. 103(7):1809-1818.

Simmons and Torok-Storb (1991) "CD34 Expression by Stromal Precursors in Normal Human Adult Bone Marrow" Blood 78(11):2848-2853.

Singer et al (1987) "Simian Virus 40-Transformed Adherent Cells From Human Long-Term Marrow Cultures: Cloned Cell Lines Produce Cells with Stromal and Hematopoietic Characteristics" Blood 70(2):464-474.

Singer et al (1984) "Evidence for a Stem Cell Common to Hematopoiesis and its In Vitro Microenvironment: Studies of Patients with Clonal Hematopoietic Neoplasia" Leuk. Res. 8(4):535-545.

Spaggiari et al (2006) "Mesenchymal Stem Cell-Natural Killer Cell Interactions: Evidence that Activated NK Cells are Capable of Killing MSCs, Whereas MSCs can Inhibit IL-2-Induced NK-Cell Proliferation" Blood 107(4):1484-1490.

Stacey et al (2000) "Randomised Double-Blind Placebo Controlled Trial of Topical Autologous Platelet Lysate in Venous Ulcer Healing" Eur. J. Vasc. Endovasc. Surg. 20:296-301.

Terstappen et al (1991) "Sequential Generations of Hematopoietic Colonies Derived From Single Nonlineage-Committed CD34+CD38—Progenitor Cells" Blood 77(6):1218-1227.

(56) References Cited

OTHER PUBLICATIONS

Toba et al (1999) "Novel Technique for the Direct Flow Cytofluorometric Analysis of Human Basophils in Unseparated Blood and Bone Marrow, and the Characterization of Phenotype and Peroxidase of Human Basophils" Cytometry 35(3):249-259.

Tondreau et al (2004) "Isolation of BM Mesenchymal Stem Cells by Plastic Adhesion or Negative Selection: Phenotype, Proliferation Kinetics and Differentiation Potential" Cyrotherapy 6(4):372-379.

Tosh et al (2002) "Conversion of Pancreatic Cells to Hepatocytes" Biochem. Soc. Trans. 30:51-55.

Ueda et al (2007) "Induction of Senile Osteoporosis in Normal Mice by Intra-Bone Marrow-Bone Marrow Transplantation from Osteoporosis-Prone Mice" Stem Cells 25(6):1356-1363.

Weber (1988) "Infectious Damage to the Intervertebral Disk-Before and Following Discotomy" Z. Orthop Ihre Grenzeb 126(5):555-562 (German, English Abstract Only)

Willems et al (Jun. 2004) "Lumbar Discography: Should we Use Prophylactic Antibiotics? A Study of 435 Consecutive Discograms and a Systematic Review of the Literature" J. Spinal. Disord. Tech. 17(3):243-247.

Willheim et al (1995) "Purification of Human Basophils and Mast Cells by Multistep Separation Technique and mAb to CDw17 and CD117/c-kit" J. Immunological Methods 182:115-129

Xaymardan et al (2004) "Platelet-Derived Growth Factor-AB Promotes the Generation of Adult Bone Marrow-Derived Cardiac Myocytes" Circ Res. 94(5):E39-E45

Xian and Foster (2006) Current Stem Cells Research and Therapy 1:213-229 "Repair of Injured Articular and Growth Plate Cartilage Using Mesenchymal Stem Cells and Chondrogenic Gene Therapy".

Yamada et al (2003) "Bone Regeneration Following Injection of Mesenchymal Stem Cells and Fibrin Glue with a Biodegradable Scaffold" J. Cranio-Maxillofac. Surg. 31:27-33

Yang et al (1994) "Cardioprotective Effects of Platelets Against Ischaemia-Reperfusion Injury are Related in Part to Platelet Glutathione Redox Cycle" Cardiovasc. Res. 28(10):1586-1593 Abstract.

Ye et al (2007) "Effect of Three Growth Factors on Proliferation and Cell Phenotype of Human Fetal Meniscal Cells" Chinese Journal Reconstructive Surgery 21(10):1137-1138 with English Abstract.

Zhu et al (2001) "Recombinant Human Acidic Fibroblast Growth Factor Accelerates the Healing of Full—Thickness Dermal Wounds in Pigs" Modern Rehabilitation 5(9):31 with English Abstract.

Zhu et al (2006) "Hypoxia and Serum Deprivation-Induced Apoptosis in Mesenchymal Stem Cells" Stem Cells 24:416-425.

\* cited by examiner

COMPOSITIONS AND METHODS FOR CARTILAGE REPAIR

RELATED APPLICATIONS

This application is a continuation of U.S. patent application Ser. No. 12/922,436, filed on Oct. 25, 2010, entitled "Compositions and Methods for Cartilage Repair", now abandoned, which application is a 35 U.S.C. §371 national phase application of PCT/US2009/037126 (WO 2009/114785), filed on Mar. 13, 2009, entitled "Compositions and Methods for Cartilage Repair", which application claims the benefit of U.S. Provisional Application Ser. No. 61/036,551, filed on Mar. 14, 2008, each of which is incorporated herein by reference in its entirety.

TECHNICAL FIELD

The invention generally relates to compositions and methods for cartilage repair in patients in need thereof. More particularly, the invention relates to autologous compositions and methods for inducing chondrogenesis at sites in need of cartilage repair in patients in need thereof.

BACKGROUND

Mesenchymal stem cells are pluripotent blast or embryonic-like cells located in blood, bone marrow, dermis and periosteum. In general, these cells are capable of renewing themselves over extended periods of time as well as, under various environmental conditions, differentiating into cartilage, bone and other connective tissue. Recently, various investigators have researched the potential for using these cells to repair or regenerate target tissues, e.g., bone, cartilage, etc. In this manner MSCs have been reported to have regenerative capabilities in a number of animal models. See Acosta et al. (2005) Neurosurg Focus 19(3):E4; Barry (2003) Novartis Found Symp. 249:86-102, 170-4, 239-41; Brisby et al. (2004) Orthop Clin. North Am. 35(1):85-89; Buckwalter and Mankin (1998) Instr Course Lect. 47:487-504; Caplan (1991) J Orthop Res. 9(5):641-650.

Recently, Centeno et al. (U.S. patent application Ser. No. 11/773,774) described a method for expanding MSC's using a growth channel and autologous platelet lysate. Also described were methods for transplanting certain levels of growth factors (platelet lysate or platelets) with the expanded MSC's to the area in a patient in need of repair. The levels of these growth factors were based on a percentage of platelet lysate needed to optimally expand the cells ex-vivo.

MSC's can readily differentiate in culture depending on cytokine exposure, environmental conditions (pressure, attachment opportunities, passage treatment, etc. . . . ), or other chemical exposure. For example, exposure to varying levels of TGF-beta, FGF, and/or PDGF can all have impacts on the final cell phenotype produced in culture. In addition, leaving cells in culture longer also has impacts on differentiation potential. Cells can be cultured for a certain visual morphology, confluence, or density, all of which has an impact on the final cell product produced and its potential for certain types of tissue repair.

In replacing or repairing tissue with MSC's, one concern is the use of autologous or non-autologous cells. While MSC's have been traditionally considered immune privileged, recent investigations have demonstrated their activation of the natural killer cell system in a foreign host. (Spaggiari, Capobianco et al. 2006) This makes the use of non-autologous cells difficult, as it is anticipated that the host's immune system will attack these foreign cells and potentially decimate the population of transplanted MSCs, thus severely limiting their repair capabilities.

There is a need in the art for MSC expansion techniques that do not use drugs or growth factors which are not FDA approved and can be effectively used to replace tissue in a patient in need thereof. This is especially true where the tissue in the patient in need of repair is cartilage. Cartilage repair is a major issue in health care which will only continue to increase as the median age in the United States continues to increase.

There is a need for autologous techniques to yield MSC and non-MSC based cartilage repair techniques.

The present invention is directed toward overcoming one or more of the problems discussed above.

SUMMARY OF THE EMBODIMENTS

The present invention provides repair compositions for facilitating repair and/or replacement of cartilage in patients in need thereof. Repair compositions include an effective amount of a platelet-based material in combination with one or more chondrogenesis inducing agents. In some cases the platelet-based material and/or the chondrogenesis inducing agent(s) are autologous.

Aspects of the platelet-based material include one or more of the following solutions: platelet lysate, platelet rich plasma, platelet rich fibrin, and/or whole cell platelet concentrate.

Aspects of the chondrogenesis inducing agent include growth factors, cytokines, steroid hormones and nutrients for facilitating cartilage formation in patients in need thereof. One or more agents are combined with the platelet-based material. Chondrogenesis inducing agents can be autologous to the patient.

Repair compositions of the invention can further include cell-based materials, including: mesenchymal stem cells, chondrocytes, isolated bone marrow nucleated cells, chondrocyte progenitor cells, osteoblasts, embryonic stem cells, or stem cells of other lineages. Cells are typically autologous to the patient, being harvested from the patient prior to cartilage repair and expanded to sufficient numbers for optimal treatment.

Repair compositions of the invention can also include carrier materials, including: gels, hydrogels, absorbable polymers, and the like. Carriers act as scaffolding for cartilage formation within the site of cartilage repair. Carriers can be added to the site of repair contemporaneously with the repair compositions or be part of the repair composition.

The present invention provides pharmaceutical compositions for use in therapeutic applications. Pharmaceutical compositions herein are used to treat patients having a site in need of cartilage repair, in some cases the patient has osteoarthritis or other like degenerative disease.

The present invention provides kits having one or more of the following materials: one or more platelet based material, one or more chondrogenesis inducing agent(s), one or more cell based material and one or more carrier. In some aspects the kit includes the materials necessary to harvest the target material from a patient rather than the material itself, for example the tools and supplies necessary to harvest and prepare a platelet lysate. Kits may include vials, tissue culture flasks, culture medium, and other like laboratory materials necessary for the harvest and isolation of materials necessary to practice the present invention.

The present invention also provides methods for facilitating cartilage repair or replacement in a patient in need thereof.

Methods include harvesting and preparing a platelet-based material, for example a 5% to 40% platelet lysate, from a patient having a cartilage repair site in need of treatment; optionally harvesting and preparing a chondrogenesis inducing agent from the same patient, e.g., isolating IGF-1 from the patient, and/or obtaining and administering a non-autologous chondrogenesis inducing agent (such as dexamethasone, ascorbic acid, etc. . . . ); optionally harvesting and preparing a cell-based therapy from the same patient, e.g., harvesting and isolating mesenchymal stem cells from the patient's bone marrow, and/or obtaining and administering a non-autologous cell based material; optionally obtaining a carrier material; administering to the repair site a repair composition of the invention; monitoring and re-administering repair compositions of the invention to patient's that require additional treatment for cartilage repair.

These and various features and advantages of the invention will be apparent from a reading of the following detailed description and a review of the appended claims.

DETAILED DESCRIPTION

Definitions

The following definitions are provided to facilitate understanding of certain terms used frequently herein and are not meant to limit the scope of the present disclosure.

"About" refers to a +/−10% variation from the nominal value. It is to be understood that such variation is always included in any given value provided herein, whether or not it is specifically identified.

"Chondrogenesis inducing agent" refers to any agent capable of inducing or facilitating cartilage formation above the levels of cartilage formation found in a normal and untreated subject. Chondrogenesis inducing agents include but are not limited to; growth factors, cytokines, hormones, and various essential nutrients. Illustrative growth factors include Transforming Growth Factor-beta (TGF-β), Fibroblast Growth Factors (FGFs), Insulin Like Growth Factors (IGFs), Bone Morphogenic Protiens (BMPs); illustrative cytokines including Cytokine-like 1 (Cytl1); illustrative hormones include Human Growth Hormone (HGH); and Testosterone and illustrative essential nutrients include Ascorbic Acid, pyruvate, and amino acids. A chondrogenesis inducing agent can include one or more of the materials as described above, for example a combination of TGF-β and pyruvate.

"Mesenchymal stem cells" or "MSCs" refers to multipotent stem cells capable of differentiating into osteoblasts, chondrocytes, myocytes, adipocytes, neuronal cells, pancreatic islet cells, and the like. Additionally, methods and compositions detailing MSCs as described in U.S. Pat. Nos. 5,486,359, 6,387,367 and 5,197,985 are incorporated by reference herein in their entirety. In more detail, mesenchymal stem cells are multipotent stem cells located in the bone marrow, peripheral blood, adipose tissue and other like sources. Source MSCs of the invention can be harvested from the iliac crest of the patient in need (or other source such as the IVD, periosteum, synovial fluid, or the vertebral body or pedicle) of the restorative/replacement therapy (or a suitable donor), such patient is referred to herein as a "patient in need or patient in need thereof" (note that other sources, such as adipose tissue, synovial tissue, and connective tissue have recently been identified and are also considered as MSC sources within the scope of the present invention). In one embodiment, approximately 10-100 cc of bone marrow is harvested and "isolated" using methods described in U.S. Patent Application 60/761,441 to Centeno or through adherence to plastic, as described in U.S. Pat. No. 5,486,359 to Caplan et al. Each of these references is incorporated herein in their entirety for all purposes.

"Platelet lysate" refers to the combination of natural growth factors contained in platelets that have been released through lyses of the platelets. Lyses can be accomplished through chemical means (i.e., $CaCl_2$), osmotic means (use of distilled $H_2O$), or through freezing/thawing procedures. Platelet lysates of the invention can also be derived from whole blood and can be prepared as described in U.S. Pat. No. 5,198,357, which is incorporated by reference herein.

"Repair" refers to restoration of some or all of a surface's cartilage to an acceptable operating condition. In some instances this may entail a 5%, 10%, 15%, 20%, 25%, 30%, 35%, 40%, 45%, 50%, 55%, 60%, 65%, 70%, 75%, 80%, 85%, 90%, 95%, 100%, and 100+% increase over the untreated condition in the patient in need of cartilage repair.

"Whole cell platelet concentrate", "platelet rich plasma", and "platelet rich fibrin" are as generally known in the art. For example, platelet rich plasma or PRP can be obtained through methods as described in Landesberg et al., J Oral Maxillogac Surg 58:297, 2000, which is incorporated by reference in its entirety.

ASPECTS OF THE INVENTION

Aspects of the present invention provide cartilage repair compositions for facilitating cartilage repair in a patient in need thereof. Embodiments include a therapeutically effective amount of platelet lysate in conjunction with one or more chondrogenesis inducing agents. In some cases the platelet lysate is an autologous platelet lysate. In some cases the chondrogenesis inducing agent is an autologous chondrogenesis inducing agent.

In one embodiment, a repair composition includes a therapeutically effective amount of one or more of a platelet rich plasma, platelet rich fibrin, or a whole cell platelet concentrate in conjunction with one or more chondrogenesis inducing agents. The platelet rich plasma, platelet rich fibrin and/or whole cell platelet concentrate can be autologous. In some cases the platelet rich plasma, platelet rich fibrin and/or whole cell platelet concentrate can replace the platelet lysate. For purposes of the invention, any one or more of platelet lysate, platelet rich plasma, platelet rich fibrin and/or whole cell platelet concentrate will be referred to as a platelet-based material.

In another embodiment, the repair composition includes a therapeutically effective amount of a combination of a platelet lysate and two or more of platelet rich plasma, platelet rich fibrin or whole cell platelet concentrate in conjunction with one or more chondrogenesis inducing agent(s). As above, either or both of the platelet lysate and two or more of platelet rich plasma, platelet rich fibrin or whole cell platelet concentrate can be autologous. In some embodiments the chondrogenesis inducing agent(s) is also autologous.

In still another embodiment, a repair composition of the invention herein includes from about 10,0000 to 10,000,000,000 mesenchymal stem cells. In typical cases the mesenchymal stem cells are autologous and prepared per methods described in the definition section above or as described in U.S. patent application Ser. No. 11/773,774 (and U.S. Provisional Patent Application No. 61/014,987), which are incorporated herein by reference. Alternatively, about from 10,000 to 10,000,000,000 chondrocytes can be combined with repair compositions of the invention, chondrocytes can be autologous. Autologous chondrocytes can be isolated and expanded using techniques as described herein for MSCs as well as through a review of the relevant art, e.g., Johnson et al., Tissue Engineering, 2004 10(9-10) 1308-1318, incorporated herein by reference. In other embodiments the mesenchymal stem cells or chondrocytes are non-autologous and purchased from a vendor. In general, any combination of cells useful for inclusion in the repair compositions herein will be referred to as cell-based materials.

As such, repair compositions as described herein can include one or more of the following: autologous or non-autologous platelet-based material(s); autologous or non-autologous chondrogenesis inducing agent(s); and autologous or non-autologous cell-based materials(s).

Other aspects of the present invention provide methods for facilitating cartilage repair in a patient in need thereof.

Methods include, administering a repair composition (e.g., platelet lysate and chondrogenesis inducing agent) of the invention to a site in a patient in need of such therapy. Methods herein would include preparation of the repair composition as either a autologous composition or non-autologous composition. Where any one component of the repair composition is from a non-autologous source (excluding excipients, solutions, e.g., sterile PBS, and other materials required to administer the repair composition) the entire composition is considered non-autologous.

In another embodiment, the components that make up a repair composition can be administered sequentially, for example, the platelet lysate (and/or platelet rich plasma, platelet rich fibrin and/or whole cell platelet concentrate) and chondrogenesis inducing agent can be administered in a non-contemporaneous manner, for example within one minute of each other, within ten minutes of each other, within one hour of each other, within one day of each other or within one week of each other. Method embodiments herein include any administration procedure that results in the components of the repair composition being administered to the site in need of repair, as long as the administration is directed at repair of the same site in need of repair in the patient in need of repair.

In still other embodiments of the present invention, methods can include preparing platelet lysate solutions, platelet rich plasma, platelet rich fibrin and/or whole cell platelet concentrates from the patient in need of treatment. These platelet based materials are then autologous to the patient in need of therapy. Methods for isolating and preparing these materials are described in U.S. patent application Ser. No. 11/773,774 and U.S. Provisional Patent No. 61/014,987, which are incorporated herein by reference for all uses.

As noted above, in some embodiments herein, mesenchymal stem cells are administered in a therapeutic amount to the site in need of cartilage repair either contemporaneously or non-contemporaneously with the repair compositions of the invention.

Cartilage Repair Compositions

In more detail, composition embodiments of the invention include cartilage repair compositions having an enhanced capacity for cartilage repair in a patient in need thereof. Cartilage repair composition embodiments in accordance with the invention include various combinations of: platelet lysate solution, platelet rich fibrin, platelet rich plasma, and whole cell platelet concentrate with one or more chondrogenesis inducing agent(s). Chondrogenesis inducing agents include various growth factors, cytokines, hormones and nutrients that have been shown to induce or facilitate cartilage growth in the in vivo or in vitro setting.

In some embodiments, the platelet lysate solution, platelet rich fibrin, platelet rich plasma and/or whole cell platelet concentrate are autologous to the patient receiving the repair composition. In other embodiments, the chondorgenesis inducing agent(s) is also autologous to the patient receiving the repair composition.

Autologous platelet-based materials are harvested and prepared as described in U.S. patent application Ser. No. 11/773,774, incorporated herein by reference for all uses. Autologous chondrogenesis inducing agents are obtained per the target agent, for example, growth factors like BMP-7 and BMP-2 can be purchased from Stryker, Inc and Medtronic, cytokines like etanercept (TNF-alpha inhibitor) can be purchased from Amgen/Wyeth, Inc, and the like.

In typical embodiments the repair compositions include stem cell or cartilage cell growth enhancing compositions of autologous platelet lysate solution. The platelet lysate solution of the invention is typically from about 5% to about 40% platelet lysate, and more typically between about 5% and 20% platelet lysate. Optimal levels of platelet lysate for any given patient can be determined based on bioavailability and concentrations of growth factors in the patients lysate. Optimal levels can be determined by reference to U.S. patent application Ser. No. 11/773,774, incorporated herein by reference for all purposes.

Typical chondrogenesis inducing agents herein include growth factors that induce or facilitate cartilage growth. Growth factors include: fibroblast growth factor, insulinlike growth factor-1, transforming growth factor-beta, bone morphogenetic protein-2, human growth hormone, PDGF-BB, and the like. (see for example: Cassiede et al., J Bone Miner Res., 1996. 11(9): p. 1264-73; Miyata et al., J Cell Physiol., 2005. 204(3): p. 948-55; Kawamura et al., Exp Hematol., 2005. 33(8): p. 865-72; Zhang et al., J Huazhong Univ Sci Technolog Med Sci., 2004. 24(3): p. 275-8; Toh et al., Growth Factors, 2005. 23(4): p. 313-21; Chrisman, O. D., Clin Orthop Relat Res., 1975 (107): p. 232-8; Denko et al., Semin Arthritis Rheum, 2005. 35(1): p. 24-34, each of which is incorporated by references for all purposes herein). Illustrative amounts of chondrogenesis inducing agents include: 1-100 ng/ml (1-500 nM) dose of corticosteroid, 1-500 ng/ml of TGF-beta, 1-500 nM Ascobic Acid (1-500 mg/ml), FGF-2 of 1-100 ng/mL, 10-500 ng/mL of IGF-I.

Other typical chondrogenesis inducing agents herein can include cytokines that induce or facilitate cartilage growth. Illustrative cytokines include: interleukin-1 (IL-1) and Cytokine-like 1 (Cytl1). Typical chondrogenesis inducing agents herein can also include steroid hormones like corticosteroid, human growth hormone, testosterone.

Note also that typical chondrogenesis inducing agents herein can include various cartilage inducing nutrients, for example: glucosamine, hyaluronic acid, (Zhu et al., Stem Cell 2005, incorporated by reference herein for all purposes), collagen, glycoaminoglycans, amino acid mixtures, sodium pyruvate, ascorbic acid, carbohydrates, and the like. (Cassiede et al.; Miyata et al.; Kawamura et al.; Zhang et al.; Toh et al.; Bosnakovski et al., Biotechnol Bioeng., 2006. 93(6): p. 1152-63; Derfoul et al., Osteoarthritis Cartilage, 2007. 15(6): p. 646-55; Song et al., Cytotherapy, 2004. 6(6): p. 596-601, each of which is incorporated by reference in its entirety for all purposes.). In some embodiments, combinations of one or more types of chondrogenesis inducing agents are combined with the platelet-based solutions of the invention, for example: a growth factor in combination with a cytokine, a growth factor in combination with a nutrient, or other like combinations.

In one embodiment, an about 5% to 40% platelet lysate solution is combined with one or more chondrogeneis inducing agents. Illustrative chondorgenesis inducing agent combinations include IGF-1 and corticosteroid with or without collagen. Platelet lysate with 50 ng/ml of dexamethasone, platelet lysate with ascorbic acid, dexamethasone, and pyrate, and the like.

In other repair composition embodiments, mesenchymal stem cells are combined with the platelet-based solutions and chondrogenesis inducing agents of the invention. Mesenchymal stem cells are typically autologous and can be harvested and expanded from the patient in need thereof by the methods described above. In alternative embodiments, chondrocytes are combined with the platelet-based solutions and chondrogenesis inducing agents of the invention. Chondrocytes are typically autologous and can be harvested and expanded from the patient in need thereof. In some embodiments a mix of mesenchymal stem cells and various differentiated forms of mesenchymal stem cells (up to and including chondrocytes) are combined with the platelet-based solutions and chondrogenesis inducing agents. Regardless of the nature of the cells, they can be expanded prior to implantation into the patient in need thereof in accordance with aspects of the present invention.

In still other repair compositions, a carrier material is added to modify the capacity of the embodiments to remain at the site of injury or the timing of release of the composition into the site of injury. Illustrative carriers include: gels, hydrogels, foams, or like materials. These carriers can be combined with the platelet-based materials and chondrogenesis inducing agents with or without cell additives, e.g., mesenchymal stem cells, chondrocytes, etc of the invention. In some aspects the carriers are incorporated as a scaffolding for cell additives or for endogenous cells (generally mesenchymal stem cells or chondrocytes) at or close to the site of injury.

As noted previously, repair compositions can be administered to a site in need of repair as a single composition or sequentially, where each component of the composition is added at an appropriate time to maximize repair.

Methods of Inducing or Facilitating Cartilage Repair in a Patient in Need Thereof Embodiments of the invention include therapeutic methods for restoring cartilage at a site in need of repair in a patient in need thereof. For purposes of the invention a site in need of repair is any site in a mammal, e.g., human, horse, dog, etc., in need of cartilage repair or replacement. An illustrative site is a knee joint in a patient having osteoarthritis.

In one embodiment, an initial determination is made as to what type and how much repair composition would be effective in treating the site in need of repair. This determination is based on site of repair, age of patient, autologous or non-autologous platelet-based lysate, type and amount of chondrogenesis inducing agent, etc. A determination is also made as to the timing of delivery of the different aspects of the repair composition. For example, chondrogenesis inducing agents can be selected for their capacity for degranulation of platelets at an optimal time after administration to the patient. The correct timing in such case must be determined, especially where the platelet-based composition is administered at a time zero and the chondrogenesis inducing agent, e.g., cytokine, is administered at a time X, X representing the optimal time at which to have administered platelet materials degranulate. Various aspects of this initial determination are described in PCT application PCT/US2008/087452, Compositions and methods to promote implantation and engraftment of stem cells, which is incorporated by reference herein for all purposes.

Once the above determinations have been made, methods herein require administration of repair compositions of the invention to the patient in need thereof. Administration to the site in need of repair can be accomplished through a surgical incision, arthroscopically, or percutaneously.

Administration may be performed one or more times in order to maximize cartilage repair or replacement. Injury site analysis can be performed to ensure that acceptable results have been achieved.

Therapeutic Applications

Repair compositions of the invention provide optimal cartilage repair and/or replacement conditions/environment to repair a site in a patient in need thereof.

Repair compositions herein can be formulated as pharmaceutical compositions and administered to a patient in need thereof, typically a mammalian, including a human patient. Repair compositions can be formulated in a variety of forms adapted for the chosen route of administration.

For administration of the compositions of the invention as an injectable solution (whether it be through a surgical incision or arthroscopically), compositions can be formulated according to techniques well-known in the art, using suitable dispersing or wetting agents, such as sterile oils, including synthetic mono- or di-glycerides and fatty acids, including oleic acid.

Solutions or suspensions of the repair compositions can be prepared in water, isotonic saline (PBS), and optimally mixed with an nontoxic surfactant. Dispersions may also be prepared in glycerol, liquid polyethylene, glycols, vegetable oils, triacetin and mixtures thereof. Under customary use and storage conditions, the repair compositions herein may contain one or more preservatives to prevent growth of microorganisms.

"Therapeutic applications" herein refers to use of the compositions and methods of the invention to treat a patient having a site in need of cartilage repair or replacement. In some embodiments, the inventions disclosed herein include therapeutic applications in patients having disease states that limit the inherent ability of the patient to repair or re-grow cells at the repair site. For example, patient's that have osteoarthritis.

The description of the present invention has been presented for purposes of illustration and description, but is not intended to be exhaustive or limiting of the invention to the form disclosed. The scope of the present invention is limited only by the scope of the following claims. Many modifications and variations will be apparent to those of ordinary skill in the art. The embodiment described and shown in the figures was chosen and described in order to best explain the principles of the invention, the practical application, and to enable others of ordinary skill in the art to understand the invention for various embodiments with various modifications as are suited to the particular use contemplated.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims. All references cited herein are incorporated in their entirety by reference.

1. Cassiede, P., et al., *Osteochondrogenic potential of marrow mesenchymal progenitor cells exposed to TGF-beta 1 or PDGF-BB as assayed in vivo and in vitro*. J Bone Miner Res, 1996. 11(9): p. 1264-73.
2. Miyata, T., et al., *Platelet-derived growth factor-BB (PDGF-BB) induces differentiation of bone marrow endothelial progenitor cell-derived cell line TR-BME2 into mural cells, and changes the phenotype*. J Cell Physiol, 2005. 204(3): p. 948-55.

3. Kawamura, K., et al., *Adenoviral-mediated transfer of TGF-beta1 but not IGF-1 induces chondrogenic differentiation of human mesenchymal stem cells in pellet cultures.* Exp Hematol, 2005. 33(8): p. 865-72.
4. Zhang, Y., et al., *In vitro chondrogenic phenotype differentiation of bone marrow-derived mesenchymal stem cells.* J Huazhong Univ Sci Technolog Med Sci, 2004. 24(3): p. 275-8.
5. Toh, W. S., et al., *Combined effects of TGFbeta1 and BMP2 in serum-free chondrogenic differentiation of mesenchymal stem cells induced hyaline-like cartilage formation.* Growth Factors, 2005. 23(4): p. 313-21.
6. Chrisman, O. D., *The effect of growth hormone on established cartilage lesions. A presidential address to the Association of Bone and Joint Surgeons,* 1974. Clin Orthop Relat Res, 1975(107): p. 232-8.
7. Denko, C. W. and C. J. Malemud, *Role of the growth hormone/insulin-like growth factor-1 paracrine axis in rheumatic diseases. Semin Arthritis Rheum,* 2005. 35(1): p. 24-34.
8. Zhu, H., et al., *The Role of the Hyaluronan Receptor CD44 in MSC Migration in the Extracellular Matrix.* Stem Cells, 2005.
9. Bosnakovski, D., et al., *Chondrogenic differentiation of bovine bone marrow mesenchymal stem cells (MSCs) in different hydrogels: influence of collagen type II extracellular matrix on MSC chondrogenesis.* Biotechnol Bioeng, 2006. 93(6): p. 1152-63.
10. Derfoul, A., et al., *Glucosamine promotes chondrogenic phenotype in both chondrocytes and mesenchymal stem cells and inhibits MMP-13 expression and matrix degradation.* Osteoarthritis Cartilage, 2007. 15(6): p. 646-55.
11. Song, L., D. Baksh, and R. S. Tuan, *Mesenchymal stem cell-based cartilage tissue engineering: cells, scaffold and biology.* Cytotherapy, 2004. 6(6): p. 596-601.

All references herein are incorporated by reference for all purposes.

What is claimed is:

1. A method for facilitating cartilage repair in a patient in need thereof comprising:
   obtaining platelets from the patient;
   preparing a 5% to 40% platelet lysate solution from the platelets, wherein said platelet lysate solution is prepared by freeze-thawing the platelets obtained from the patient;
   obtaining autologous mesenchymal stem cells (MSCs) from bone marrow, peripheral blood, or adipose tissue of the patient;
   obtaining one or more chondrogenesis inducing agents; and
   administering the MSCs, the 5% to 40% platelet lysate solution and the one or more chondrogenesis inducing agents to a site in the patient in need of cartilage repair;
   wherein the combined administration of the MSCs, the 5% to 40% platelet lysate solution and the one or more chondrogenesis inducing agents facilitates cartilage repair at the site in the patient in need of repair, and wherein at least one of the chondrogenesis inducing agents is a corticosteroid.

2. The method of claim 1, further comprising administering a platelet rich plasma, platelet rich fibrin, whole cell platelet or a mixture thereof to the patient in need thereof, and wherein the administration is at the site in the patient in need of repair.

3. The method of claim 1 wherein the administering step further comprises administering a carrier material comprising a gel, hydrogel, or foam.

4. The method of claim 1, wherein the corticosteroid is dexamethasone.

5. The method of claim 1, wherein the MSCs, the 5% to 40% platelet lysate solution and the corticosteroid are combined prior to administration to the patient.

6. The method of claim 1, wherein the corticosteroid and the 5% to 40% platelet lysate solution are combined prior to administration to the patient.

* * * * *